US006316524B1

(12) United States Patent
Corzani et al.

(10) Patent No.: US 6,316,524 B1
(45) Date of Patent: *Nov. 13, 2001

(54) DISPOSABLE ABSORBENT ARTICLE FOR TOPICAL ADHESIVE ATTACHMENT TO THE SKIN OF A WEARER

(75) Inventors: Italo Corzani, Chieti; Mario Romano, Pescara, both of (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/331,688

(22) PCT Filed: Dec. 22, 1997

(86) PCT No.: PCT/US97/23451

§ 371 Date: Jun. 23, 1999

§ 102(e) Date: Jun. 23, 1999

(87) PCT Pub. No.: WO98/27909

PCT Pub. Date: Jul. 2, 1998

(30) Foreign Application Priority Data

Dec. 23, 1996 (EP) .................................................. 96120738
Jul. 1, 1997 (EP) .................................................. 97110727

(51) Int. Cl.[7] .............................. A61F 13/15; C08L 53/02
(52) U.S. Cl. ............................ 523/111; 524/505; 604/389
(58) Field of Search .................................. 524/270, 277, 524/322, 481, 505, 578; 442/149; 525/95; 523/105, 111; 428/343 R, 355, 354; 604/389

(56) References Cited

U.S. PATENT DOCUMENTS

| 4,369,284 | 1/1983 | Chen . | |
|---|---|---|---|
| 4,460,364 | 7/1984 | Chen et al. . | |
| 4,589,876 | * 5/1986 | Van Tilburg | 604/385 R |
| 5,057,571 | 10/1991 | Malcolm et al. . | |
| 5,360,855 | 11/1994 | Gobran . | |
| 5,559,165 | 9/1996 | Paul . | |
| 6,156,818 | * 12/2000 | Corzani et al. | 523/111 |
| 6,177,482 | * 1/2001 | Cinelli et al. | 523/111 |

FOREIGN PATENT DOCUMENTS

| 0 611 575 A1 | 8/1994 | (EP) . |
|---|---|---|
| WO 95/10576 | 4/1995 | (WO) . |
| WO-95/ 16424-A | * 6/1995 | (WO) . |
| WO 96/13238 | 5/1996 | (WO) . |

* cited by examiner

Primary Examiner—Edward J. Cain
Assistant Examiner—Katarzyna Wyrozebski-Lee
(74) Attorney, Agent, or Firm—Peter D. Meyer

(57) ABSTRACT

The invention is a disposable absorbent article for topical adhesive attachment to a wearer. The article has a wearer facing surface and a garment facing surface and comprises an absorbent core. The article comprises an adhesive on at least the wearer facing surface. The adhesive has a dynamic elastic behaviour so that the difference between G'37 at a frequency of 1 rad/sec and G'37 at a frequency of 100 rad/sec is not greater than 150% of G'37 at a frequency of 1 rad/sec. The adhesive has a dynamic viscous behavior so that the difference between G"37 at a frequency of 1 rad/sec and G"37 at a frequency of 100 rad/sec is not greater than 10,000 Pa. The ratio G'37 over G"37 in the frequency range 1–100 rad/s is greater or equal to 3.3.

16 Claims, No Drawings

DISPOSABLE ABSORBENT ARTICLE FOR TOPICAL ADHESIVE ATTACHMENT TO THE SKIN OF A WEARER

FIELD OF THE INVENTION

The present invention relates to disposable absorbent articles particularly sanitary napkins, pantiliners, adult incontinence products or sweat pads. In particular the present invention relates to such disposable absorbent articles which are worn by direct attachment to the skin of the wearer in the area were absorption of bodily liquids is desired.

BACKGROUND OF THE INVENTION

The prior art in the field of disposable absorbent articles for topical application to the skin of a wearer is particularly developed in the field of band-aids, plasters and bandages. These articles are, however, typically applied in an emergency situation where for example a cut into the skin of the wearer has occurred and absorption of the body liquids emanating from a wound is desired. In this context performance aspects of the absorbent article such as comfortable and easy use and application, painless removal, discreteness are subordinate to criteria such as sterility, healing support, mechanical protection of the wound. Also such wound covering absorbent articles are mostly used in skin areas where prior to application of the absorbent article body hair can be removed or where little or no hair grows.

The present invention does not relate to wound covering absorbent articles but relates to absorbent articles for absorption of body liquids which naturally emanate from a body without a wound. For example sanitary napkins or pantiliners for use in the genital region are such articles. Also incontinence devices which are worn e.g. in the genital region or sweat pads which are worn in the arm pit region of a person are the subject of the present invention.

Such articles are applied to the skin of a wearer in a region were typically a considerable amount of hair grows such that the criteria of easy and painless removal of the article is of key importance. Such articles have generally been disclosed in US statutory invention registration H1602 or WO 96/33683. Some more details of such articles have been considered for example in PCT application WO 95/16424. In this document sanitary articles having a body adhesive which is applied on the wearer facing side of a sanitary napkin along the entire periphery are disclosed. The problem underlying this document is primarily the safe attachment to the skin but mentions also the problems of detachment of such articles after use without causing undue pain to a wearer.

The disclosure of WO 95/16424 includes a detailed analysis of the criteria for the body adhesive in respect to Theological criteria. However, this document has little regard to the problem of painless removal of such articles since the rheological criteria taught include epilatory, i.e. hair removal, compositions which are commercially available such as STREP MIELE (TM) sold in Italy by Laboratori Vaj S.p.A. The adhesives for topical attachment mentioned in WO 95/16424 include also today's pressure sensitive adhesives which are used to attach sanitary napkins to undergarments. Further, this document only identifies static rheological characteristics but is silent as to the dynamic rheological behaviour of a body adhesive.

In WO 96/13238 a frequency dependent body adhesive model is disclosed. However, all measurements disclosed, e.g. on page 9, were made at temperatures between −60° C. and +120° C. and at actual frequencies of 0.1 to 100 rad/s. In order to obtain the necessary data at application temperature (about 20° C., typical bath room, i.e. storage temperature) the Williams-Landel-Ferry (hereinafter WLF) equation was used.

This WLF equation is empirical and only valid within certain limits e.g. it cannot be used to extrapolate to temperatures below the glass transition temperature of a polymeric adhesive also the WLF cannot be used on the basis of values obtained below the glass transition temperature. Details about the WLF equation and its applicability can be found in "Principles of Polymer processing" by Z. Tadmor and C. G. Gogos, published by John Wiley & Sons or in "Viscoelastic Properties of Polymers" by J. D. Ferry also published by John Wiley & Son. Since this is already missing from WO 96/13238 the applicability of the disclosed data cannot be assessed.

European Patent Application EP-638 303 discloses the use of a body adhesive on side cuffs of sanitary napkins in order to keep the cuffs in an upright position. Swiss publication CH-643730 discloses the use of a very long sanitary napkin having chamfered outer edges with a body adhesive at the four corners of the outer edges in order to provide a body adhesive area well outside the region of pubic hair growth.

Based on the above state of the art it is an objective of the present invention to provide disposable absorbent articles for absorption of natural emanating liquids from the body of a wearer which are attached to the skin of a wearer while providing painless removal of the absorbent article. It is another objective of the present invention to ensure upon removal of the absorbent article that no residual adhesive remains on the skin or on the hair of the wearer. It is another objective of the present invention to provide disposable absorbent articles which are worn in such close proximity to the liquid emanating area of the wearer that liquid losses to the outside of the absorbent article is minimised or eliminated. For disposable absorbent articles worn in the crotch region of a wearer this will translate into an improved security against soiling of the surrounding skin tissue and clothing.

In addition to the above objectives of the present invention it is also desirable for sanitary napkins, pantiliners and catamenial devices to reduce or even eliminate odour emanating from the product since its application to the skin of the wearer provides an odour seal which prevents odours of the absorbed liquid or forming from the absorbed liquid to reach beyond the absorbent article.

BRIEF DESCRIPTION OF THE INVENTION

The present invention relates to disposable absorbent articles for topical adhesive attachment to a wearer of such articles. The article typically has a wearer facing surface and an outside surface also called garment facing surface in the context of articles worn underneath clothing. The article comprises an absorbent core structure between the wearer facing surface and the garment facing surface for absorbing liquids naturally emanating from a wearer. The disposable absorbent article according to the present invention comprises on at least part of the wearer facing surface an adhesive for topical adhesive attachment of the article to the skin of the wearer.

The adhesive is particularly characterized by having an elastic modulus at a temperature of 37° C. (100° Farenheit) abbreviated $G'_{37}$ and having a viscous modulus at a temperature of 37° C. (100° Farenheit) of $G''_{37}$. The adhesive is selected to have a dynamic elastic behavior such that the difference between $G'_{37}$ at a frequency of 100 rad/sec and $G'_{37}$ at a frequency of 1 rad/sec is not greater than 150%, preferably 80%, of $G'_{37}$ at 1 rad/sec or preferably less than 10000 Pa. The adhesive further is selected to have a dynamic viscous behavior such that the difference between $G''_{37}$ at a frequency of 100 rad/sec and $G''_{37}$ at a frequency of 1 rad/sec is not greater than 10000 Pa, preferably not greater than 5000 Pa, most preferably not greater than 1000 Pa.

It is particularly preferred that the articles according to the present invention have a value of the ratio $G'_{37}$ over $G''_{37}$ in the whole frequency range from 1 to 100 rad/sec of greater or equal to 1, preferably greater or equal to 1.6 and most preferably greater or equal to 3.3.

The value of the ratio $G'_{37}$ over $G''_{37}$ at least for the frequency range 1 to 100 rad/sec can change with increasing frequency, while not necessarily being proportional to the frequency change. This ratio of $G'_{37}$ over $G''_{37}$ should not change within the frequency range by a factor of more than 3, preferably more than 2, and most preferably should stay constant.

At 1 rad the preferred value of $G'_{37}$ is below 20000 Pa, preferably below 15000 Pa and most preferably even less than 10000 Pa. On the other hand the value of $G''_{37}$ at a frequency of 1 rad/sec should not exceed 15000 Pa, it should preferably be less than 10000 Pa and most preferably even less than 5000 Pa. The above rheological criteria can be satisfied by adhesive compositions where the composition comprises from 51 % to 99.5 % of a plasticising compound or composition which is liquid at 20° C., from 0.5 to 20%, preferably 5% to 15%, of a polymeric compound or composition which is soluble or swellable in the plasticising compound or composition and with a tackifying resin in an amount in the range from 0% to 600% by weight of the polymeric compound. The plasticising compound or composition is preferably selected from the group consisting of water, alcohols, preferably glycerol, glycols, polyglycols, liquid polybutenes, oil or combinations thereof while the polymeric compound or composition is preferably selected from the group consisting of block-copolymer-thermoplastic-elastomers, styrene-block-copolymers and hydrogenated styrene-block-copolymers.

Quite generally the preferred body adhesive is at least partially hydrophobic, preferably 60%, more preferably 80%, by weight of the adhesive consist of hydrophobic components and most preferably none of the materials in the adhesive are hydrophilic, i.e. it is made totally from hydrophobic components.

In a particularly preferred embodiments according to the present invention the adhesive covers less than 20% or even more preferably less than 10% of the wearer facing surface of the absorbent article. The present invention is most beneficially applied in the field of sanitary napkins or pantiliners.

DETAILED DESCRIPTION OF THE INVENTION

This invention relates to disposable absorbent articles which are applied directly to the skin of a user. The article exhibits absorbency for bodily fluids, the protection of the user's garments from soiling, improved physical comfort to the user, and is easy to produce and to package. The disposable absorbent article is described below by reference to a sanitary napkin or catamenial, however panty liners, adult incontinence articles or sweat pads are also included under the term disposable absorbent articles. The term "sanitary napkin", as used herein, refers to an article which is worn by females adjacent to the pudendal region and which is intended to absorb and contain the various body fluids which are discharged from the body (e.g., vaginal discharges, menses, and/or urine) and which is intended to be discarded after a single use. The disposable absorbent article is preferably thin, more preferably between 1 and 5 mm thick and either substantially flat prior to use or in a preshaped form.

The terms "joined" or "affixed", as used herein, encompasses configurations whereby a first member is directly connected to a second member and configurations whereby a first member is indirectly connected to a second member by connecting the first member to intermediate members which in turn are connected to the second member.

In a preferred embodiment a sanitary napkin of the present invention comprises a liquid pervious topsheet, a liquid impervious backsheet joined to the topsheet, and an absorbent core intermediate the topsheet and the backsheet. The sanitary napkin has two main surfaces, a body contacting or wearer facing surface, and a garment facing or contacting surface.

The topsheet is compliant, soft feeling, and non-irritating to the wearer's skin. The topsheet also can have elastic characteristics allowing it to be stretched in one or two directions in portions of the topsheet or throughout its extension. Further, the topsheet is fluid pervious permitting fluids (e.g., menses and/or urine) to readily penetrate through its thickness. A suitable topsheet can be manufactured from a wide range of materials such as woven and non woven materials; polymeric materials such as apertured formed thermoplastic films, apertured plastic films, and hydroformed thermoplastic films; and thermoplastic scrims. Suitable woven and non woven materials can be comprised of natural fibers (e.g., wood or cotton fibers), synthetic fibers (e.g., polymeric fibers such as polyester, polypropylene, or polyethylene fibers) or from a combination of natural and synthetic fibers or bi-/multi-component fibers.

Preferred topsheets for use in the present invention are typically selected from high loft nonwoven topsheets and apertured formed film topsheets. Apertured formed films are especially preferred for the topsheets because they are pervious to body exudates and yet non absorbent and have a reduced tendency to allow fluids to pass back through and rewet the wearer's skin. Thus, the surface of the formed film that is in contact with the wearer remains dry, thereby reducing body soiling and creating a more comfortable feel for the wearer. Suitable formed films are described in U.S. Pat. Nos. 3,929,135; 4,324,246; 4,342,314; 4,463,045; and 5,006,394. Particularly preferred micro apertured formed film topsheets are disclosed in U.S. Pat. Nos. 4,609,518 and 4,629,643. A preferred topsheet for the present invention comprises the formed film described in one or more of the above patents and marketed on sanitary napkins by The Procter & Gamble Company of Cincinnati, Ohio as "DRI-WEAVE".

Topsheets having not a homogeneous distribution of liquid passage ways but only a portion of the topsheet comprising liquid passage ways are also contemplated by the present invention. Typically such topsheets would have the liquid passage ways oriented such that they result in a centrally permeable and peripherally impermeable topsheet for liquids.

The wearer facing surface of the formed film topsheet can be hydrophilic so as to help liquid to transfer though the topsheet faster than if the body surface was not hydrophilic.

In a preferred embodiment, surfactant is incorporated into the polymeric materials of the formed film topsheet such as is described in PCT-publication WO 93/09741. Alternatively, the wearer facing surface of the topsheet can be made hydrophilic by treating it with a surfactant such as is described in U.S. Pat. No. 4,950,254.

Another alternative are so called hybrid topsheets which incorporate fibrous and film like structures particularly useful embodiments of such hybrid topsheets are disclosed in PCT publications WO 93109744; WO 93/11725 or WO 93/11726.

When referring to the topsheet a multi layer structure or a mono layer structure is contemplated. The hybrid topsheet mentioned above is such a multi layer design but other multi layer topsheets such as primary and secondary topsheet designs are also considered.

The absorbent structure or absorbent core can include the following components: (a) optionally a primary fluid distribution layer preferably together with a secondary optional fluid distribution layer; (b) a fluid storage layer; (c) optionally a fibrous ("dusting") layer underlying the storage layer; and (d) other optional components.

a Primary/Secondary Fluid Distribution Layer

One optional component of the absorbent structure according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilised. The fluid distribution layers can be comprised of any material typical for such distribution layers. In particular fibrous layers which maintain the capillaries between fibers even when wet are useful as distribution layers.

b Fluid Storage Layer

Positioned in fluid communication with, and typically underlying the primary or secondary distribution layers, is a fluid storage layer. The fluid storage layer can comprise any usual absorbent material or combinations thereof. It preferably comprises absorbent gelling materials usually referred to as "hydrogel", "superabsorbent", hydrocolloid" materials in combination with suitable carriers.

The absorbent gelling materials are capable of absorbing large quantities of aqueous body fluids, and are further capable of retaining such absorbed fluids under moderate pressures. The absorbent gelling materials can be dispersed homogeneously or non-homogeneously in a suitable carrier. The suitable carriers, provided they are absorbent as such, can also be used alone.

Suitable absorbent gelling materials for use herein will most often comprise a substantially water-insoluble, slightly cross-linked, partially neutralised, polymeric gelling material. This material forms a hydrogel upon contact with water Such polymer materials can be prepared form polymerizable, unsaturated, acid-containing monomers which are well known in the art.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins/panty liners.

An embodiment of the absorbent structure made according to the present invention comprises a double layer tissue laminate formed by folding the tissue onto itself. These layers can be joined to each other. Absorbent gelling material or other optional material can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orion), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the absorbent gelling material is dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing absorbent gelling materials partially or fully.

c Optional Fibrous ("Dusting") Layer

An optional component for inclusion in the absorbent structure according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent structure. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent structure according to the present invention can include other optional components normally present in absorbent webs. For example, a reinforcing scrim can be positioned within the respective layers, or between the respective layers, of the absorbent structure. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

Another component which can be included in the absorbent structure according to the invention and preferably is provided close to or as part off the primary or secondary fluid distribution layer are odor control agents. Active carbon coated with or in addition to other odor control agents, in particular suitable zeolite or clay materials, are optionally incorporated in the absorbent structure. These components can be incorporated in any desired form but often are included as discrete particles.

The backsheet primarily prevents the exudates absorbed and contained in the absorbent structure from wetting articles that contact the absorbent product such as underpants, pants, pyjamas and undergarments. The backsheet is preferably impervious to liquids (e.g. menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions.

The backsheet typically extends across the whole of the absorbent structure and can extend onto and form part of the topsheet by folding around the absorbent structure. Thereby a topsheet configuration as disclosed in U.S. Pat. No. 4,342,314, column 16, lines 47–62 can be achieved without the requirement to selectively aperture the topsheet.

The backsheet can comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils).

Exemplary polyethylene films are manufactured by Clopay Corporation of Cincinnati, Ohio, under the designation P18-1401 and by Ethyl Corporation, Visqueen Division, of Terre Haute, Ind., under the designation XP-39385. The backsheet is preferably embossed and/or matte finished to provide a more clothlike appearance.

Preferably, the backsheet also provides breathability to the absorbent article by being at least water vapour permeable, preferably air permeable, however, without compromising the main function of the backsheet. The backsheet can be a laminate material e.g. of a combination of microporous film, non-woven material, and/or apertured formed film. Breathability if desired can be limited to the periphery of the backsheet or it can be across the whole backsheet.

Adhesive for Topical Attachment

The articles according to the present invention as said above is applied directly to the skin of the user. In particular, sanitary napkins are applied in the genital region of a typically female user around the area of liquid discharge. The word "skin" according to the present invention does not only relate to the specific derma of the user but include the mucous tissue as well as the hair which is typically found in the genital region of users of sanitary napkins.

In order to provide fixation of the article according to the present invention to the skin of the user it is necessary to provide a certain area on the topsheet side of the article which is facing the wearer with the adhesive for topical attachment also referred to as body adhesive.

Various designs in this respect are contemplated but preferably the body adhesive is provided along the peripheral edge of the topsheet such that a central area of the article is left without adhesive. This will most appropriately facilitate placing the article such that the liquid permeable topsheet without adhesive on it is placed adjacent the bodily liquid emanating orifice such that emanating liquid is immediately transported into the absorbent structure of the absorbent article without the possibility of leakage or spillage.

It is, however, not necessary that the body adhesive is provided in a closed circle around the periphery of the topsheet but it can be provided in incremental areas such as dots or discrete lines such that decoupling between the different places of attachment is providing additional comfort to the wearer of such articles.

In order to satisfy the objectives according to the present invention the following should be considered.

Physical, Rheological and Adhesive Characteristics of a Body Adhesive

Even so body adhesives are used like pressure sensitive adhesives on human skin hair and mucous tissues, it is understood that the body adhesive compositions could only with difficulty be considered typical pressure sensitive adhesives (referred to as PSA hereinafter) on the basis of the most characteristic rheological behaviours identifying such materials.

In fact as the person skilled in the art of adhesives knows, the most characteristic feature that distinguish a PSA from other substances that can temporarily stick things (as e.g. water could) is the fact that their rheological parameters and especially the Elastic Modulus G' vary greatly with the frequency of applied stresses. More in particular, G' of PSA can increase over some orders of magnitude while the frequency of applied stresses varies from typical bonding frequency to typical debonding frequency, i.e. 1 rad/s to 100 rad/s as indicated below.

As a first consequence, it derives that it is inadmissible to define materials intended for use as "adhesives" by giving values of rheological parameters and especially of G' at a fixed value of frequency. This can be misleading because in the absence of other characteristics it may lead to include materials which have no practical value. It is hence believed that rheological characterisation must be on the base of dynamic considerations.

This not only applies to the Elastic Modulus G' but also to the viscous modulus G" and hence also for $\tan(\delta)=G''/G'$. It is well known that typical PSA have not only a high variation of G' across the considered frequencies but also there is an even higher variation of G" which can get close or become even higher than the value of G', i.e. $\tan(\delta)$ becomes about or even greater than 1, in particular at the frequencies that are typical of the debonding.

Without wishing to be bound by theory this can be interpreted as meaning that a high fraction of the energy applied for the debonding is dissipated in internal frictions (so it is not effective in causing the debonding) while this fact causes macroscopically the recording of a very high level of adhesive force.

In order to provide good conditions of bonding, i.e. at a frequency of about 1 rad/sec, the absolute values of the elastic modulus should not be too high, otherwise the adhesive is too hard and it is not able to intimately join or mold to the surface to which it is expected to adhere. It is also important to have a low absolute value of G" in order to have good cohesion which is particularly valuable for a direct application on the human body while the material remains soft and capable of gently adhering to the skin.

Finally the person skilled in the art will also recognise that the Glass Transition Temperature Tg of the PSA is a parameter which is useful to more fully define completely the group of useful PSA materials.

As indicated above materials useful as body adhesives according to the present invention have rheological characteristics which are measured at a reference temperature of 37° C. as body temperature and in a range of frequencies. It has been found that upon application of an article with a body adhesive the adhesive contact is formed at a low frequency, while debonding happens at the speed of removing the article. This speed is expressed as a frequency of 100 rad/s while the low frequency of forming the adhesive bond has been found to be on the order of 1 rad/s. Therefore, the frequency range for use according to the present invention is between 1 and 100 rad/s. The following set of characteristics should be satisfied:

in the range of frequencies the percent variation of the elastic modulus $G'_{37}$ is lower or equal to 150%, preferably lower than 100% and more preferably lower than 80%, of $G'_{37}$ at 1 rad/s, preferably the variation is less than 10000 Pa in absolute terms. This is met by the body adhesive exemplified below while e.g. Promeon RG-63B, quoted in the prior art, shows in the same range of frequencies a variation of $G'_{37}$ of 331% which is not acceptable according to the present invention.

in the range of frequencies the variation of the viscous modulus $G''_{37}$ is not greater than 10000 Pa, preferably not greater than 5000 Pa, most preferably not greater than 1000 Pa.

the value of the ratio $G'37/G''37$ at least for the frequency range 1 radis to 100 rad/s should preferably be unity or above, more preferably 1.6 or above and most preferably 3.3 or above, while preferably not exceeding about 50.

It should be noted that G' and G" at the application frequency of 1 rad/s are taken at a temperature of 37° C. In practical use of articles according to the present invention the actual storage temperature of the article and hence the temperature of the body adhesive upon application varies widely. E.g. storage in a hot bathroom near a radiator could reach up to about 37° C., while storage in a storage room or in a bathroom without heating but with an open window during winter could be close to 0° C. However, since the article according to the present invention is used directly on skin and the wearer typically would not want to apply a too cold article the actual temperature of the body adhesive will reach 37° C. very quickly or even be warmed up by the wearer prior to application. Hence it is believed that the adhesive bonding characteristics are selected most appropriately at body temperature.

As indicated above the Theological behaviour can also be related to the values of the Glass Transition Temperature Tg. For body adhesives according to the present invention Tg should preferably be less than −15° C., more preferably less than −20° C. and most preferably less than −25° C.

Chemical and Compositional Characteristics of a Body Adhesive

In order to satisfy the requirements of the above Theological and physical characteristics of a body adhesive the following formulation criteria can be used in addition. It should be noted that the most of the compositions useful as body adhesive have a substantially gel-like structure and are preferably gels. This derives from the fact that:

the prevailing component is a material liquid at room temperature a macromolecular or polymeric component is present in minor quantities vs the plasticiser. It forms, in the preferred embodiments, a three dimensional network caused by physical or chemical links between the molecules. Particularly useful physical links are the ones present in systems containing Block Thermoplastic Elastomers.

More specifically, the compositions comprise:

from 0.5 to 20%, preferably 5% to 15%, by weight of a macromolecular polymeric substance or a mixture of such substances soluble or swellable in the below mentioned plasticiser(s). As not limiting examples such macromolecular or polymeric substances can be natural and/or synthetic such as natural gums or derivatives such as natural gums and gelatines, their derivatives and alginates; polyacrilics; polyvinyl alcohol; polyethylene oxide; polyvinylpyrrolidon (PVP) or polyvinylethers, their copolymers and derivatives; cellulose derivatives; Block Copolymer Thermoplastic Elastomers and preferably Styrenic Block Copolymers and more preferably the hydrogenated grades Styrol/Ethylene-Butylene/Styrol (SEBS), Styrene/Isoprene/Styrene (SIS), and Styrol/Ethylene-Propylene/Styrol (SEPS).

from 51 to 99.5% by weight of a plasticising substance or a mixture of plasticising substances, which are liquid at room temperature. As non-limiting examples the plasticiser can be water, various alcohols (like in particular glycerol), glycols, polyglycols, liquid polybutenes, natural or synthetic oils such as vegetable oils, mineral oils, or combinations thereof.

from 0 to 600% by weight of the macromolecular polymeric substance of a tackifying resin whose main scope is to tailor the Tg especially in systems based on synthetic polymers.

from 0 to 10% and more preferably form 0 to 5% by weight of substances for facilitating and stabilising the gelation both of hydrophilic or hydrophobic liquid plasticisers. These may be for oily systems, e.g. the fatty acids of $C_8$ to $C_{22}$, their metallic salts and their polyoxo-derivatives; lanolin derivatives; silica; bentonite, montmorillonite and their derivatives; polyamides, waxes or mixtures thereof.

Common additives known in the art as preservatives, antioxidants, anti UV, pigments, mineral fillers, rheology modifiers etc. can also be comprised in quantities up to 10% each.

When chemical crosslinks are formed in the system, a crosslinking agent can be present preferably in quantities up to 5% by weight. Chemical crosslinking can be formed also by mutual neutralisation of polymers having different functionalities as in the reaction between acid polyacrylics and polysaccharides.

The resulting compositions for body adhesives can be divided into three families according to the nature of the main component, i.e. the liquid plasticiser(s):

1) Hydrophobic compositions in which the plasticiser is typically an oil or blend of oils of vegetable or mineral origin and the polymer is usually a synthetic polymer, preferably an elastomer, soluble or swellable in oil(s).

2) Mixed phase compositions in which both hydrophobic and hydrophilic components, possibly in both plasticisers and polymers, form two or more separate phases. In such cases an emulsifier/surfactant is preferably present at a suitable level to form stable emulsions between the incompatible phases. For body adhesives according to the present invention it is preferably that the hydrophobic components are prevailing vs. the hydrophilic ones.

3) Hydrophilic compositions in which typically the plasticiser is water/glycerol/glycols and the like and/or mixtures thereof and the polymeric phase is of synthetic (e.g. polyacrilics) or natural (e.g. natural gums) origin or mixtures thereof.

It is to stress that, differently from what is already known in the medical field and from the cited prior art, the hydrophilic compositions are not preferred while the hydrophobic and mixed phases compositions 1) and 2) are preferred in the applications of the present invention.

This depends partially on technical reasons in the sense that many hydrophilic compositions used in the medical field show too low elastic character and cohesion for being useful in the present application. The other reason to prefer hydrophobic or mixed phase compositions is that the application of the present invention in particular in the sanitary napkin field will include a probability of contacting the body adhesive with the liquid to be absorbed. Since the liquid to be absorbed are all of a general aqueous kind contact with a hydrophilic body adhesive would result in a certain absorption of the bodily liquids into the body adhesives.

This would then have the result of changing the Theological characteristics and therefore the functionality of the body adhesive, causing a non-hygienic appearance but also would cause the bodily liquids to remain in direct skin contact over an extended period which is typically not desired by any of the disposable absorbent articles according to the present invention. In addition this may also constitute a potential drawback for the user, since some hydrophilic compositions are potentially good culture media for the growth of many micro-organisms including even pathogens.

Further hydrophilic body adhesive also tend to be perceived as cold and wet which upon application of a fresh sanitary napkin or an underarm sweat pad is not in line with typical consumer expectation. Additional problems result from the fact that in particular body adhesives comprising water as the plasticiser have a tendency to dry out unless they are sealed into an impermeable package.

Absorbent articles according to the present invention can be made by any of the ways usual in the art. The application of the adhesive to the topsheet side of the absorbent article should not cause major problems to those skilled in the art since it can be provided by similar techniques as is commonly used for a panty fastening adhesive. The total area of the wearer facing surface of the absorbent article which is covered by body adhesive should be not more than 20%, preferably not more than 10%. Preferably, the adhesive is close to the periphery of the absorbent article and in the case of film topsheets (or when the backsheet is folded onto the topsheet) the adhesive is preferably on a portion of the film which is not permeable to liquids.

The body adhesive on the article (as is common with panty fastening adhesives) needs to be protected prior to use. This protection can be provided by a release liner such as a siliconised or surfactant treated paper, provided this paper is a good release surface for the particularly selected body adhesive.

In principle the absorbent article according to the present invention is supported on the wearer by the body adhesive and does not require additional support to remain in place. However, it is possible to provide for example a sanitary napkin with a skid resistant coating on the backsheet side in order to prevent the sanitary napkin form gradually migrating out of position. Also even though panty fastening adhesives are not desired and hence not preferred according to the present invention they are not strictly speaking excluded in the context of the present invention.

EXAMPLE 1

An oil based composition useful in the present invention was compounded using 9.9% by weight of Kraton G-1651, a Styrene/Ethylene-Butylene/Styrene block copolymer containing 33% by weight styrene and available from Shell Co, and 59.3% by weight of Kaydol, a paraffinic mineral oil available from Witco Co.

Moreover the composition contained 301 parts of tackifying resin per 100 parts of Kraton polymer. The tackifying resin was Escorez 5300, a hydrogenated resin available from Exxon Co.

Magnesium Stearate, available from Carlo Erba S.p.A., was used a a co-gelifying agent for oil at a level of 0.7% by weight.

Irganox 1010, an antioxidant available from Ciba-Geigy, was added at a level of 0.3% by weight.

So finally the formulation had the following percent composition:

| | |
|---|---|
| Kraton G-1651 | 9.9% by weight |
| Kaydol | 59.3% by weight |
| Escorez 5300 | 29.8% by weight |
| Magnesium Stearate | 0.7% by weight |
| Irganox 1010 | 0.3% by weight |

The composition showed the following rheological properties at 37° C.

a) Elastic Modulus at 1 rad/s, $G'_{37}$=6876 Pa b) Ratio between Elastic and Viscous Modulus at 1 rad/s, $G'_{37}/G''_{37}$=12.49 Ratio between Elastic and Viscous Modulus at 100 rad/s, $G'_{37}/G''_{37}$=7.01 c) The ratio $G'_{37}$ at 100 rad/s over $G'_{37}$ at 1 rad/s was 1.308.

The above formulation was judged as comfortable for application on sensitive, hairy skin.

Comparative Example

A componotine oil based composition was compounded using 7.1% by weight of Kraton G-1651, a Styrene/Ethylene-ButylenelStyrene block copolymer containing 33% by weight styrene and available from Shell Co, and 41.9% by weight of Kaydol, a paraffinic mineral oil available from Witco Co.

Moreover the composition contained 704 parts of tackifying resin per 100 parts of Kraton polymer. The tackifying resin was Regalrez 3102, a hydrocarbon resin available from Hercules Co.

Magnesium Stearate, available from Carlo Erba S.p.A., was used a a co-gelifying agent for oil at a level of 0.7% by weight.

Irganox 1010, an antioxidant available from Ciba-Geigy, was added at a level of 0.3% by weight.

So finally the formulation had the following percent composition:

| | |
|---|---|
| Kraton G-1651 | 7.1% by weight |
| Kaydol | 41.9% by weight |
| Regalrez 3102 | 50.0% by weight |
| Magnesium Stearate | 0.7% by weight |
| Irganox 1010 | 0.3% by weight |

The composition showed the following rheological properties at 37° C.

a) Elastic Modulus at 1 rad/s, $G'_{37}$=3059 Pa b) Ratio between Elastic and Viscous Modulus at 1 rad/s, $G'_{37}/G''_{37}$=2.53 Ratio between Elastic and Viscous Modulus at 100 rad/s, $G'_{37}/G''_{37}$=0.74 c) The ratio $G'_{37}$ at 100 rad/s over $G'_{37}$ at 1 rad/s was 4.944

The above formulation was judged as highly uncomfortable for application on fore-arm skin. Application to sensitive hairy skin was unacceptable.

What is claimed is:

1. Disposable absorbent article for topical adhesive attachment to a wearer of said article said article having a wearer facing surface and a garment facing surface and comprising an absorbent core between said wearer facing surface and said garment facing surface wherein said article comprises on at least part of said wearer facing surface an adhesive for said topical adhesive attachment of said article, said adhesive having an elastic modulus at a temperature of 37° C. (100° F.), $G'_{37}$, and having a viscous modulus at a temperature of 37° C. (100° F.), $G''_{37}$, said adhesive being selected to have a dynamic elastic behaviour such that the difference between $G'_{37}$ at a frequency of 1 rad/sec and $G'_{37}$ at a frequency of 100 rad/sec is not greater than 150% of $G'_{37}$ at a frequency of 1 rad/sec, and, said adhesive being selected to have a dynamic viscous behaviour such that the difference between $G''_{37}$ at a frequency of 1 rad/sec and $G''_{37}$ at a frequency of 100 rad/sec is not greater than 10000 Pa; and, wherein the value of the ratio $G'_{37}$ over $G''_{37}$ in the frequency range 1–100 rad/s is greater or equal to 3.3.

2. Article according to claim 1 wherein the value of the ratio $G'_{37}$ over $G''_{37}$ changes with increasing frequency at least for the frequency range 1–100 rad/s and said change of G' over G'' is by a factor of 2 or less.

3. Article according to claim 1 wherein said adhesive is selected so that the difference between $G'_{37}$ at a frequency of 1 rad/sec and $G'_{37}$ at a frequency of 100 rad/sec is not greater than 10000 Pa.

4. Article according to claim 1 wherein said adhesive is selected so that the difference between $G''_{37}$ at a frequency of 1 rad/sec and $G''_{37}$ at a frequency of 100 rad/sec is not greater than 5000 Pa.

5. Article according to claim 1 wherein $G'_{37}$ is less than 20000 Pa at a frequency of 1 rad/s.

6. Article according to claim 5 wherein $G'_{37}$ is less than 15000 Pa at a frequency of 1 rad/s.

7. Article according to claim 6 wherein $G'_{37}$ is less than 10000 Pa at a frequency of 1 rad/s.

8. Article according to claim 1 wherein $G''_{37}$ is less than 15000 Pa at a frequency of 1 rad/s.

9. Article according to claim 8 wherein $G''_{37}$ is less than 10000 Pa at a frequency of 1 rad/s.

10. Article according to claim 9 wherein $G''_{37}$ is less than 5000 Pa at a frequency of 1 rad/s.

11. Absorbent article according to claim 1 wherein said adhesive is a composition of materials comprising from 51% to 99.5% by weight of a plasticising compound or composition which is liquid at 20° C.;

from 0.5% to 20% by weight of a polymeric compound or composition which is solvable or swellable in said plasticising compound or composition;

a tackifying resin in an amount of from 0% to 600% by weight of said polymeric compound or composition.

12. Absorbent article according to claim 1 wherein said plasticizing compound or composition is selected from the group consisting of water, alcohols, glycols, oil, or combinations thereof; and, said polymeric compound or composition is selected from the group consisting of block-copolymer-thermoplastic-elastomers, styrene-block-copolymers, hydrogenated styrene-block copolymers, and combinations thereof.

13. Absorbent article according to claim 11 wherein at least 80% by weight of said adhesive consist of hydrophobic components.

14. Article according to claim 1 wherein said adhesive covers less than 20% of said wearer facing surface.

15. Article according to claim 14 wherein said adhesive covers less than 10% of said wearer facing surface.

16. Article according to claim 1 which is a sanitary napkin or panty-liner.

* * * * *